(12) United States Patent
Apostol et al.

(10) Patent No.: US 8,071,379 B2
(45) Date of Patent: Dec. 6, 2011

(54) METHODS OF TISSUE ENGINEERING

(75) Inventors: Monica Apostol, Coram, NY (US);
Pernodet Nadine, Huntington, NY (US);
Mriam Rafailovich, Plainview, NY (US);
Nan-Loh Yang, Staten Island, NY (US)

(73) Assignee: ELC Management LLC, New York, NY (US)

( * ) Notice: Subject to any disclaimer, the term of this patent is extended or adjusted under 35 U.S.C. 154(b) by 848 days.

(21) Appl. No.: 12/136,543

(22) Filed: Jun. 10, 2008

(65) Prior Publication Data
US 2009/0305414 A1    Dec. 10, 2009

(51) Int. Cl.
*C12N 5/00* (2006.01)
*C08K 9/00* (2006.01)
*C08K 3/00* (2006.01)

(52) U.S. Cl. ............. 435/378; 435/395; 435/402; 524/1

(58) Field of Classification Search .................. 435/378, 435/395, 402; 524/1
See application file for complete search history.

(56) References Cited

OTHER PUBLICATIONS

Nakanishi et al. (2008) Analytical Sciences, vol. 24, 67-72.*
Kumar et al. (2005) The 229th ACS National Meeting in San Diego, CA, Mar. 13-17, 2005, BIOT 422, abstract.*
Iwasaki et al. (2007) Colloids and Surfaces B: Biointerfaces, vol. 57, 226-236.*
Riess et al. (2003) Prog. Polym. Sci., vol. 28, 1107-1170.*
Chan-Park et al. (2004) Macromol. Biosci., vol. 4, 665-673.*
Russell (2002) Science, vol. 297, 964-967.*
Levrand, et al.; "Light induced controlled release of fragrances by Norrish type II photofragmentation of alkyl phenyl ketones;" PPS Paper; www.rsc.org/pps; Oct. 2002.

* cited by examiner

*Primary Examiner* — Anne Marie S Wehbe
(74) *Attorney, Agent, or Firm* — Peter Giancana

(57) ABSTRACT

An improved substrate for growing mono-layers of adherent-type cells and methods of growing tissue structures, ex vivo. The improved substrate, which comprises a silicon substrate coated with a photo cleavable polymer, releases adherent cells non-enzymatically. Also disclosed are methods for assembling complex layers of cells of various types.

8 Claims, 3 Drawing Sheets

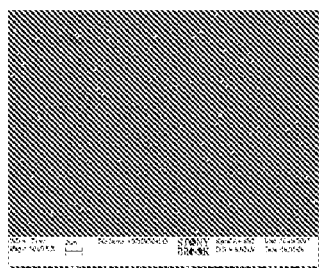 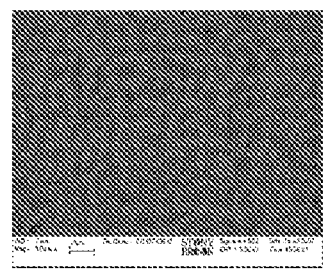
Figure 1a            Figure 1b
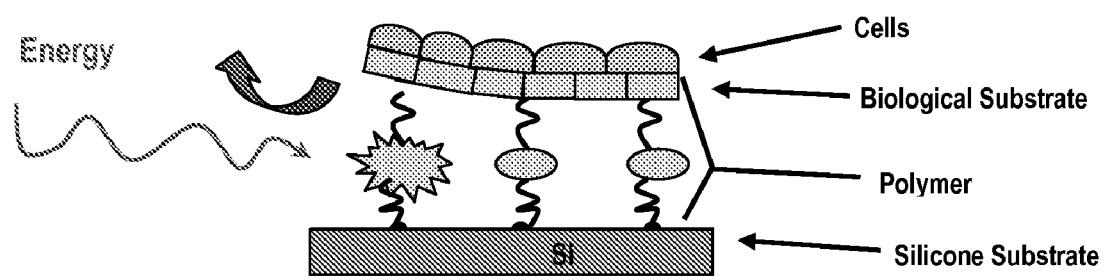
Figure 2

METHODS OF TISSUE ENGINEERING

FIELD OF THE INVENTION

The invention is in the field of tissue engineering. Specifically it pertains to methods of growing tissue structures, ex vivo. It also pertains to non-enzymatic methods of harvesting tissues that are cultured in the laboratory. It also pertains to a construct for ex vivo tissue culture.

BACKGROUND

In biology, a culture is the growing of cells or tissues outside of, and separate from, an organism. Most commonly, and herein, cell and tissue culture refer to the culturing of animal cells, as well as human cultures and cultures from plants, in vitro. Cell or tissue culturing is carried out under precisely controlled conditions, and generally requires the use of a growth medium comprising a specific serum.

Various methods of isolating cells for ex vivo culture are known. These include: purifying white blood cells from blood; breaking down extracellular matrix with enzymes (mononuclear cells); and explant culture, in which pieces of tissue are placed in a growth medium, to grow out cells that are harvested for culture. Cells that are cultured directly from a subject are known as primary cells.

Cells are cultured in an incubator where temperature, humidity, $CO_2$ content, growth medium and light exposure are carefully controlled. These parameters and their optimal values will vary, for various cell types. Some specific parameters that define a growth medium include: glucose concentration, growth factors and other nutrients, pH of the medium. One common growth medium that is suitable for human and mammalian cell types is Dulbecco's Modification of Eagles Medium (a.k.a. Dulbecco/Vogt modified Eagle's minimal essential medium, DMEM). Growth factors derived from blood may be used to supplement the growth medium.

Some cells live without attaching to a surface, and may be cultured in suspension. Cells of the bloodstream are one example. Generally, cells derived from solid tissue must be cultured on a solid substrate to which the cells adhere. Adherent culture cells may be grown on a plastic substrate. The plastic substrate may have a coating that comprises components of the extracellular matrix. Such components increase the adhesion of cells to the substrate and provide other bio-signals needed for growth. Once a viable culture is established, the culture may be further grown and prepared for re-transplantation, experimentation, transfection and trans-duction, or other purpose.

In a successful cell culture, cells proliferate by division, eventually filling up the available space. Cells in culture may be manipulated to various ends, by various methods. At some point, some cells may be removed from the culture. The particular manipulation depends on whether the culture is in suspension or adherent. For example, suspended cells may be separated from the liquid substrate by centrifuge. In contrast, adherent cells require the breaking of bonds between the cells and proteins that anchor the cells to a solid substrate. Enzymes may be used for this purpose, for example a solution of trypsin-EDTA is commonly used to effect dissociation of anchorage dependent cells from a culture surface.

One challenge faced in tissue engineering research is the ability to stack mono-layers of adherent cells, and maintain the viability of the stack as it grows into a more complex tissue.

Another important challenge faced in tissue engineering research is the ability to produce tissue constructs composed of different types of cells, wherein the constructs are similar to those that assemble naturally in the organism. To achieve this, mono-layers of different cell types would have to be harvested and assembled in a manner that approximates natural tissue growth. It would be convenient to grow mono-layers of various adherent cell types, harvest the layers individually, and then stack the layers one on top of the other, in a well defined manner. Here again, maintaining the viability of the stack of adherent cells until the layered structure can grow into a mature multi-cellular tissue, is a challenge. Thus, new substrate materials and/or a new technique for raising thin layers of adherent cells off of a substrate, are needed.

Taking it a step further, one goal is to regenerate tissues within the patient by delivering prepared cells to a specific site of damage, and then triggering controlled cell growth and differentiation. Achieving this goal will require control over the self-organization of cultured cells into specific arrangements. The implanted cells that proliferate at the site of damage must grow and align themselves precisely, in order to collectively become a functioning tissue. Without meticulous organization, the disoriented cells may interfere with the development of each monolayer of cells and prevent the growth of a comprehensive tissue or organ. Material science has developed biological constructs or scaffolds, that direct and maintain the structure of a tissue. Often, these scaffolds are created with materials that are easier to control than natural biological materials. Nevertheless, there remains a need for improved methods of growing specific arrangements of multi-cell-type tissues, into specific shapes and structures.

OBJECTIVES

A main object of the present invention is to provide an improved substrate for growing mono-layers of adherent-type cells.

Another object of the invention is to provide an improved substrate that releases adherent cells non-enzymatically or with reduced use of enzymes.

Another object is to provide methods culturing multi-layer cell structures.

Another object is to provide methods for assembling complex layers of cells of various types.

Another object is to provide methods of culturing tissues for implantation, wherein the tissues comprise complex organizations of cells of various types.

SUMMARY OF THE INVENTION

The foregoing objects are achieved in the present invention, which includes novel techniques using a silicon substrate coated with a photo cleavable polymer. The polymer is capable of functioning in the presence of growth medium for the cells, which may comprise, for example, proteins.

DESCRIPTION OF THE FIGURES

FIGS. 1a and 1b show the difference in the uniformity between an annealed and un-annealed polymer coated silicone wafer.

FIG. 2 diagrams the relationship of the silicone substrate and the photo-cleavable polymer, a portion of which acts a biological substrate.

DETAILED DESCRIPTION

Figure 3:
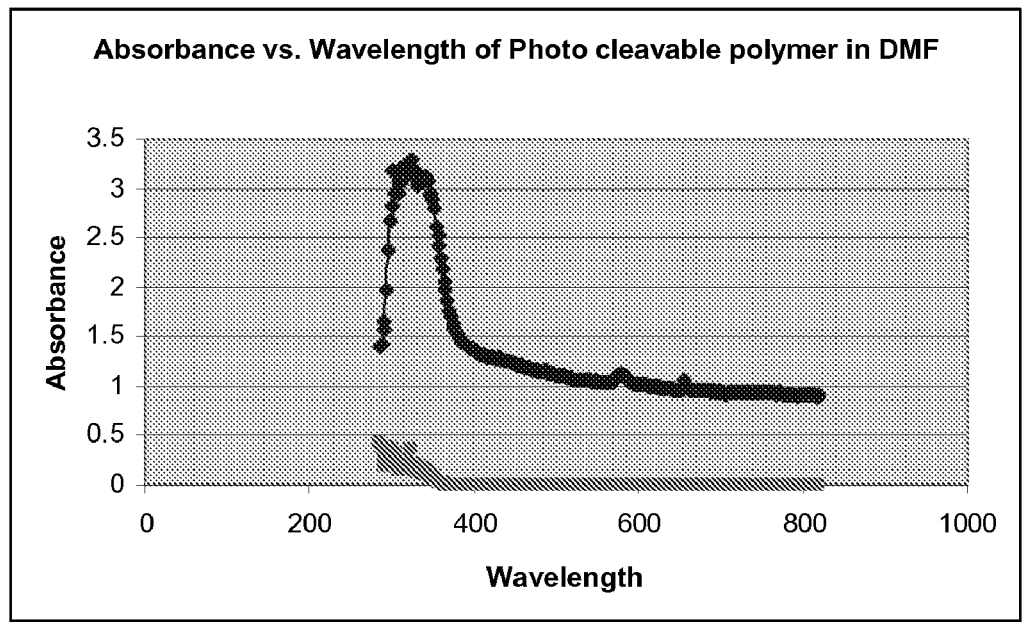
FIG. 3 shows an absorbance spectrum of UV light by the triblock copolymer, with peak absorbance at about 366 nm.

Throughout this specification, the terms "comprise," "comprises," "comprising" and the like shall consistently mean that a collection of objects is not limited to those objects specifically recited. Other definitions provided within this description, apply also to the claims.

Silicone Substrate

In the present invention the substrate is a silicone wafer coated with a photo cleavable polymer. To be a suitable substrate, the photo cleavable polymer must adhere to the silicone wafer, but must otherwise be non-reactive with the polymer under incubation conditions. Suitable silicone wafers are available from Wafer World, Inc. (West Palm Beach, Fla.). The size of the wafer may vary, but typically, range from about 25 to 100 mm$^2$.

Preparation of the Silicon Wafer

In order to use silicon wafers as a support surface, the wafers must undergo a process that eliminates any interfering substances, particles, or scratches and that renders the surface of the wafer hydrophilic. One such standard process is now described. The wafers are immersed in trichloroethylene for a period of time sufficient to remove fingerprints or any heavy residues on the wafer surface, about three minutes, for example.

After rinsing the wafers with de-ionized water, they are sonicated in methanol for a period of time sufficient to remove residual dust, about ten minutes, for example. Then, in order to remove any organic contamination, the wafers are immersed for about fifteen minutes in a freshly mixed solution of ammonium hydroxide ($NH_4OH$), hydrogen peroxide ($H_2O_2$), and de-ionized water, in 1:1:4 ratios for ten minute at 80° C.

As a post-cleaning check, the wafers are immersed, for about 30 seconds, in a solution of hydrofluoric acid and de-ionized water. They are then rinsed thoroughly with de-ionized water. This step removes $SiO_2$, but it also makes the surface hydrophobic. Therefore, the wafers are immersed for about ten minutes in a freshly mixed 1:1:4 solution of sulfuric acid ($H_2SO_4$), hydrogen peroxide ($H_2O_2$), and de-ionized water, at a temperature of about 80° C. This step removes any ionic or metallic impurities, creates a natural oxide layer and renders the surface hydrophilic. After rinsing thoroughly with de-ionized water and drying with nitrogen gas, the wafer surfaces are ready to be coated with a photo cleavable polymer. Throughout this specification "clean wafer" or "clean silicone wafer" refers to a wafer prepared as just described.

A novel feature of the present invention is that the surface of a clean silicon wafer is coated with a solution of a photo-sensitive polymer (see below). To create a thin layer film of the polymer and remove excess polymer and solvent, the wafer is spun using, for example, a Photoresist Spinner from Headway Research Inc. A useful rate of spin is about 2.05× 10$^3$ rpm, for about 30 seconds.

In at least some methods of the present invention, after the polymer is applied to a clean silicone wafer, it is treated by annealing. Annealing strengthens the bond between the silicone wafer and the photosensitive polymer and removes residual solvent. Annealing also presents a much more uniform polymer surface. (See FIGS. 1*a*, 1*b*) At least one photosensitive polymer successfully used, was annealed for 12 hours, at about 170° C., in a vacuum oven. The temperature of the annealing step cannot be so high as to damage the photosensitive polymer (i.e. by melting the polymer). Throughout this specification "coated wafer" or "coated silicone wafer" refers to a wafer with a thin, uniform layer of annealed photosensitive polymer.

Photo-Cleavable Polymer

In the present invention, a suitable photosensitive polymer is a photo-cleavable polymer. That is, one or more portions of the polymer must separate when exposed to a well defined type of light. Polymers that are photosensitive without photo-cleavage, are generally not suitable for the present invention. In use, the photo-cleavable polymer is disposed between a silicone substrate (i.e. a silicone wafer as described above) and the cells being cultured. FIG. 2 diagrams the relationship of the silicone substrate, the photo-cleavable polymer, and the cell culture. As is clear from FIG. 2, the free end of the photo-cleavable triblock copolymer acts as a substrate for the cell culture.

A set of first binding sites on a suitable photo-cleavable polymer adheres to the silicone substrate, but is otherwise non-reactive with the silicone substrate under conditions of incubation. A set of second binding sites on a suitable photo-cleavable polymer adheres to, and is biologically compatible with the cells being cultured. It is thought that adhesion between the polymer and the cells, generally occurs between cell membrane proteins and extracellular matrix proteins. The first binding sites are not generally capable of adhering to the cell membrane (i.e. cell membrane proteins) and the second binding sites are not generally capable of adhering to the silicone substrate. Otherwise, the polymer might not orient in the manner described herein.

Sufficient adhesion of the cells at the second set of binding sites must be achieved before the cells are adversely affected. Here, "sufficient adhesion" means that the plated cells remain in place on the silicon wafer after the cells are submerged in a liquid medium. Preferably, sufficient adhesion takes place within 2 hours, more preferably within 30 minutes, and most preferably within 15 minutes of plating the cells on to the coated silicone wafer. Furthermore, a suitable photo-cleavable polymer has an activation or release mechanism. When the polymer is activated it will release the cells as a complete monolayer of a single cell type.

In the present invention, these requirements have been met with a tri-block copolymer of poly[4-vinylpyridine] ($P_4VP$, which adheres to the silicon substrate); poly[vinyl phenyl ketone] (PVPK, which is a photo-cleavable with UV light); and poly[methylmethacrylate] (PMMA, which is a biocompatible polymer to which bio-compatible materials adhere).

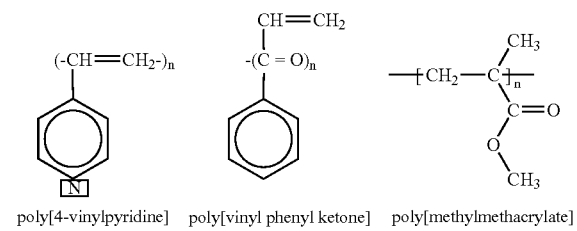

poly[4-vinylpyridine]   poly[vinyl phenyl ketone]   poly[methylmethacrylate]

As noted above, the photosensitive polymer is applied to the silicone substrate. The polymer is prepared in solution with dimethyl formamide (DMF). A usable range of concentration is about 7 to about 10 mg of polymer per mL of solvent; preferred is about 8.5 mg/mL. The poly[4-vinylpyridine] blocks bond to the surface of the silicone wafer and the PMMA blocks (free end) extend above the surface, ready to receive cells for culture.

Photo Cleavage

The mid-block of the photo cleavable tri-block copolymer is poly[vinyl phenyl ketone]. Poly[vinyl phenyl ketone] is capable of undergoing a Norrish type II photoelimination reaction. The reaction causes a scission in the =C—C backbone. Carbonyl compounds containing γ C—H bonds undergo, upon electronic excitation, characteristic 1,5-hydrogen shift to yield both cleavage and cyclization products. Phenyl ketones release terminal alkenes together with an enol.

The Norrish type II reaction is an activated process. The activation energy for PVPK is 3-3.6 Kcal/mol. The absorbance of UV light by a 8.35 mg/mL DMF solution of the triblock copolymer was measured. FIG. 3 shows the results. Peak absorbance occurs at about 366 nm, and a range of useful wavelengths is about 330-390 nm.

Testing the Photosensitivity of the Polymer

Photo-cleavable polymers that are useful in the present invention exhibit a precise, localized sensitivity to UV light. The ability to denature the polymer at specific sites, while leaving adjacent sites in tact, is a must if the polymer is going to be useful for manipulating the growth patterns of cells. The $P_4VP$-PVPK-PMMA polymer has this property.

To demonstrate that the polymer exhibits a precise, localized sensitivity to UV light, a photolithography technique may be employed. A polymer-coated silicone wafer was prepared as above. The wafer was placed in a 35 mm Petri dish. To simulate the culture environment in which cells grow, 3 mL of liquid (de-ionized water) was introduced into the dish. The polymer was exposed to UV light at wavelength 366 nm, for about four hours. Exposure was limited to four hours because at longer duration depleted the de-ionized water through evaporation. The light was provided by a UV lamp (30 watts). Exposure was done through a patterned mask (a transmission electron microscopy 500 mesh grid).

Figure 4:
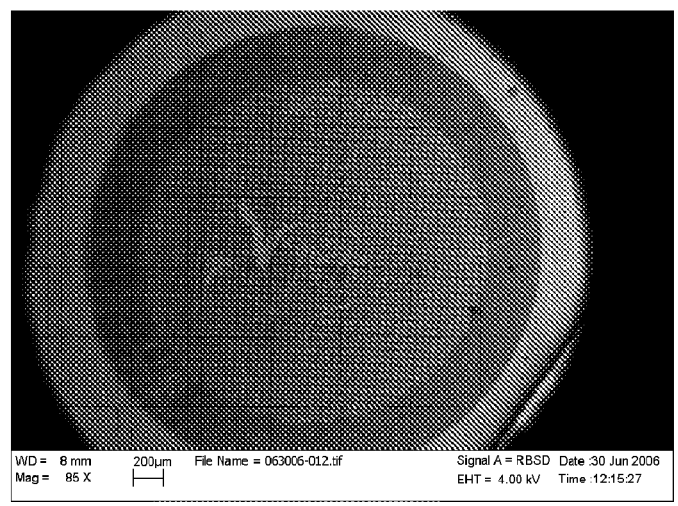
FIG. 4 shows localized sensitivity of the photo-cleavable polymer.

FIG. 4 shows the polymer after the mask was removed. As seen in the figure, the uniform pattern of the mask was reproduced in the photosensitive polymer. The dark area features are the in tact triblock copolymer. The light features indicate denatured polymer, where a biological substrate can no longer adhere.

Figure 5:
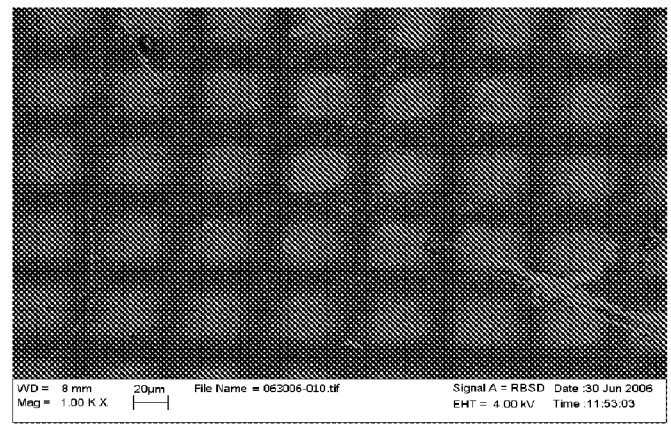
FIG. 5 shows localized sensitivity of the photo-cleavable polymer on a micron scale.

FIG. 5 was captured with a scanning electron microscope and the distance between denatured sites was determined to be about 36 μm. Thus, the polymer was denatured at specific sites, but not generally. We conclude that the polymer-silicone wafer combination is useful, not only for improved release of cells from a substrate, but for controlling the growth patterns of cells. This result also suggests treatments for diseased tissues that target only specific cells, while leaving healthy cells unharmed. This may develop into a more efficient system of treating cancerous tissue, for example.

Figure 6:
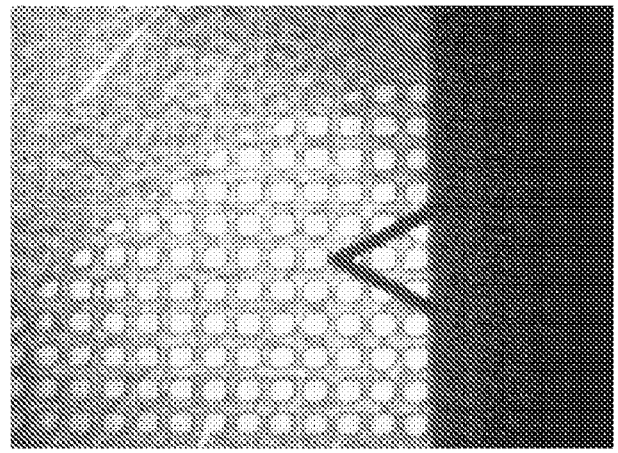
FIG. 6 is high magnification photo of the exposed polymer-coated silicone wafer sample.
Figure 7:
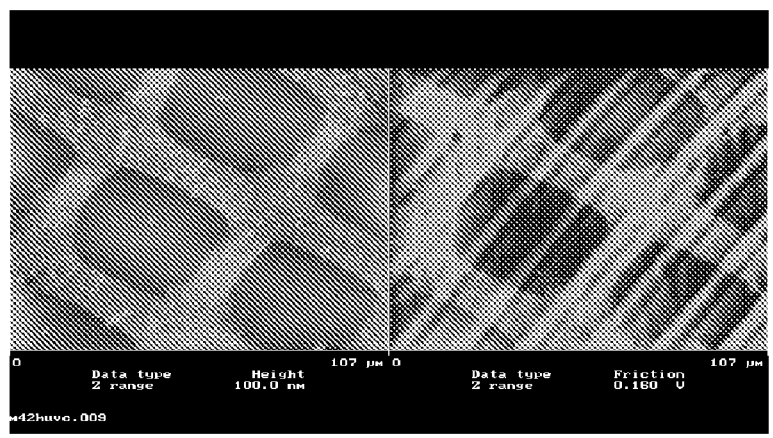
FIG. 7 shows the distinct patterning and the depth of the holes created in the photo-sensitive polymer by the UV light.

FIG. 6 is high magnification photo of the exposed polymer-coated silicone wafer sample. FIG. 7 shows the distinct patterning and the depth of the holes created by the exposure to UV light, through the TEM mask. The scale suggests that the depth is approximately 34 nm. Thus, it is determined that four hours of exposure to UVC light, causes a reaction in the polymer to a depth of about 34 nm into the polymer.

Plating the Cells and the Cell Culture Medium

Successful cultures have been grown starting with cell densities in the range of 3,000 to 100,000 cells per $cm^2$. Larger or smaller densities may be possible. The cells for plating may be harvested from their container using techniques known to a person skilled in the art. This may include using trypsin to release the cells from the surface of their container. Once the cells for plating are harvested, they are plated onto the coated silicone wafer. Once sufficient adhesion has been achieved (i.e. 15 to 30 minutes), the wafer may be placed in a Petri dish or other container. To sustain the cells and promote growth and division during incubation, a solution of nourishment is introduced into the container, submerging the silicone wafer. The solution may include, for example, proteins such as heparin or fibronectin. The solution may have various agents that encourage the division and growth of cells. Any material that sustains cell growth may be suitable for use. A material "sustains" cell growth if the material facilitates cell adhesion and cell proliferation. This may include, for example, providing nourishment and/or biological signals that encourage or participate in cell adhesion and proliferation. In practice, a coated silicone wafer is placed in a Petri dish and immersed in a 10% solution of Bovine Calf Serum in Dulbecco's Modification of Eagles Medium (DMEM) or other suitable solution. Thereafter, the cells are incubated in any fashion practiced in the art.

Removing Cells from the Wafer

After incubation, removing the cells from the silicone substrate involves breaking the photosensitive bond on the mid-block (PVPK). Ideally, the sample should be exposed to UV light for just long enough to break all the photosensitive bonds in the PVPK that are in contact with the cell sample. Using a 30 watt light source at 366 nm wavelength, a typical UV exposure time is about 15 minutes to about 30 minutes. A person of ordinary skill in the art could readily determine an appropriate exposure time to effect separation.

As noted above, the UV light causes a scission within the poly[vinyl phenyl ketone]. After separation, the monolayer of cells is still adhered to the PMMA layer, which has been acting as a substrate for the cell culture, and a portion of the PVPK midblock. Once separated, this cell-substrate complex may float in solution. Even if it does not float, the cells are easily harvested. The continued viability of the harvested cell-substrate complex has been demonstrated by incubating and culturing the cell-substrate complex in the usual manner. The cells in the complex continued to mature and multiply normally. Thus, the presence of the residual polymer causes no problem for the cell culture.

Cells

It is expected that methods of the present invention are applicable to a range of cell types, including dermal fibroblasts. In general, any adherent-type cell that is capable of being nourished from solution and that can adhere to the PMMA endblock of the photosensitive polymer may be useful. Suitable cells may be purchased from commercial sources or may come from biopsy. Cells may be mature or immature, healthy or diseased, human or animal.

Testing the UVC Sensitivity of Dermal Fibroblasts

Ultimately, methods of the present invention will expose cultured cells to UVC light. The following experiment was undertaken to demonstrate that at least some cells that are exposed to UVC light for extended periods of time, remain viable.

Plating of Cells

Sample cultures of dermal fibroblast cells were prepared in a Petri dish using 10% solution of Bovine Calf Serum in Dulbecco's Modification of Eagles Medium (DMEM) for nourishment. The incubation period was 3 days in a NAPCO 5430 incubator with 4.9% $CO_2$ and 100% humidity. The test sample cultures were raised from the Petri dish with trypsin and plated on clean silicone wafers. The cell density of the samples that were prepared in this manner, ranged from 3,000 to 100,000 cells per cm.

Change of Medium to Reduce Refraction

Initially, it was thought to expose the samples to UVC light while having the plated silicone wafers immersed in the 10% DMEM solution, to sustain the fibroblast cells. However, it was realized that the amount of refraction of the UV light by the solution posed a problem. Refracted light would make it more difficult to denature specific portions of the photosensitive polymer. If a tissue having a specific pattern of cells is to be achieved, refraction would pose a problem. For this reason, the plated silicone wafers were immersed in a phosphate buffer solution which is able to sustain the cells for the duration of the experiment and which causes no appreciable refraction of UVC light. The ions in the phosphate buffer solution provide sustenance and maintain a suitable pH for the dermal fibroblast cells. In principle, any solution that can sustain the cells for a sufficient duration, and that limits the refraction of UVC light to acceptable levels, may be suitable for use during the UV exposure procedure.

Exposure to UVC

Test samples were exposed to UVC light (366 nm) for 30 minutes, 1 hour and 2 hours. After sufficient exposure, the entire monolayer of cells detaches from the silicone wafer and floats in solution. The samples were removed from solution and examined. After exposure, the presence of healthy cells on the sample surface demonstrated that cells can survive up to 120 minutes under UVC light. Next, the cells were incubated for another 3 days in a NAPCO 5430 incubator with 4.9% $CO_2$ and 100% humidity. The incubated dermal fibroblast cells remained viable.

This experiment demonstrated that the amount of UVC exposure that is necessary to effect separation of the cell culture from the silicone wafer, does not destroy the cell culture. This experiment also demonstrates the compatibility of the silicone wafer with the triblock co-polymer, which remained anchored to the silicone through the extended UVC exposure.

Multilayered Tissue Structures

The ability to grow mono-layer cell cultures on a polymer-coated silicone substrate and the ability to release the monolayer non-enzymatically and non-destructively with UVC light, has been demonstrated. Also, the property of the triblock copolymer to denature in a localized fashion has been shown. Taken together, this means that the polymer-coated silicone wafers described herein, may be used to manufacture multilayered tissues out of mono-layer cell cultures. Thus, the present invention includes methods of assembling more complex cell structures, layer by layer. These layered structures may be homogeneous (same cell type) or heterogeneous (multi-cell type). Furthermore, mono-layers of cells harvested from a polymer-coated silicone wafer herein described, may be grown on any type of scaffold commonly used to direct the growth of tissues ex vivo.

In practice, a mono-layer of cells grown on a polymer-coated silicone wafer and released with UV light, is harvested and deposited or stacked on top of another cell mono-layer. The relative orientation of cells between mono-layers may be controlled. The exact sequence of a stack of mono-layers is controlled. It is expected that complex tissues, suitable for transplantation into a living host, may be manufactured by the methods herein described.

What is claimed is:

1. A construct for ex vivo tissue engineering comprising:
    a photo-cleavable triblock copolymer having:
        a set of first set of adhesion sites located in a poly[4-vinylpyridine] endblock;
        a set of second adhesion sites located in a poly[methyl-methacrylate] endblock; and
        a middle block of poly[vinyl phenyl ketone]
    and an silicone inorganic substrate that adheres to the copolymer at the set of first adhesion sites.

2. The construct of claim 1 wherein the inorganic substrate has a hydrophilic surface.

3. The construct of claim 2 wherein the inorganic substrate is silicone.

4. A method of preparing the construct of claim 1 for cell culture, the method comprising the steps of:
    providing a clean silicone wafer having a hydrophilic surface;
    applying a solution of the photo-cleavable polymer to the hydrophilic surface;
    spinning the silicon wafer to create a uniform film of the polymer and remove excess solvent;
    annealing the polymer to create a solid film.

5. The method of claim 4 further comprising the steps of:
    depositing viable cells onto the polymer film;
    submerging the viable cells in a solution of growth medium;
    incubating the cells for a period of time under conditions that sustain the viable cells to produce a monolayer of cells;
    exposing the construct to UV light for a time sufficient to separate the cultured monolayer of cells from the inorganic substrate.

6. A method of culturing multilayered tissues ex vivo, the method comprising the steps of:
    preparing at least two monolayers of cells according to the method of claim 5;
    arranging the monolayers in a stack, one on top of the other;
    incubating the stack for a period of time under conditions that sustain the growth of the stack.

7. The method of claim 6 wherein the monolayers of cells are homogeneous.

8. The method of claim 6 wherein the monolayers of cells are heterogeneous.

* * * * *